(12) United States Patent
Benchikh et al.

(10) Patent No.: US 8,852,953 B2
(45) Date of Patent: Oct. 7, 2014

(54) IMMUNODETECTION AND QUANTIFICATION OF PYRAZOLOPYRIMIDINE SEDATIVES

(75) Inventors: Elouard Benchikh, Crumlin Antrim (GB); Stephen Peter Fitzgerald, Crumlin Antrim (GB); Philip Andrew Lowry, Crumlin Antrim (GB); Ivan Robert McConnell, Crumlin Antrim (GB)

(73) Assignee: Randox Laboratories Ltd., Crumlin Antrim (GB)

( * ) Notice: Subject to any disclaimer, the term of this patent is extended or adjusted under 35 U.S.C. 154(b) by 204 days.

(21) Appl. No.: 13/384,278

(22) PCT Filed: Jul. 16, 2010

(86) PCT No.: PCT/GB2010/051165
§ 371 (c)(1),
(2), (4) Date: May 7, 2012

(87) PCT Pub. No.: WO2011/007180
PCT Pub. Date: Jan. 20, 2011

(65) Prior Publication Data
US 2012/0208294 A1    Aug. 16, 2012

(30) Foreign Application Priority Data

Jul. 17, 2009 (GB) .................................. 0912463.7

(51) Int. Cl.
*G01N 33/566* (2006.01)
*G01N 33/53* (2006.01)
*C07K 14/765* (2006.01)
*C07K 16/18* (2006.01)
*C07D 487/04* (2006.01)
*G01N 33/94* (2006.01)
*C07K 16/44* (2006.01)

(52) U.S. Cl.
CPC ............ *C07D 487/04* (2013.01); *G01N 33/948* (2013.01); *G01N 2430/00* (2013.01); *C07K 16/44* (2013.01)
USPC ............... 436/501; 435/7.1; 435/7.9; 435/28; 435/188; 530/389.8

(58) Field of Classification Search
None
See application file for complete search history.

(56) References Cited

PUBLICATIONS

The International Preliminary Report on Patentability, PCT/GB2010/051165, issued Jan. 17, 2012.*
Lowry et al. I, "Development of antibodies for the sensitive detection of zaleplon and related compounds," Clinical Chemistry, Jun. 2009, vol. 55, No. 6, Suppl. S, p. A257.*
Lowry et al. II, "Development of antibodies for the sensitive detection of zaleplon and related compounds," the document created on Internet on Jul. 15, 2009, and retrieved from http://www.randox-lifesciences.com/Content/useruploads/pdfs/Zaleplon%20pabs,%20AACC%202009,%20USA.pdf on Dec. 3, 2013.*
The cover pages off Supplement to Clinical Chemistry, Jun. 2009, vol. 55, No. 6, pp. A1-A286.*
A print-out retrieved from http://www.ehow.com/how_8429035_publication-date-website.html on Apr. 17, 2014.*
International Search Report for PCT/GB2010/051165 of Oct. 26, 2012.
American Association for Clinical Chemistry (AACC) News Release, Aug. 5, 2009.
Declerck, et al., Development of a radioimmunoassay for the determination of zoldipem in biological samples, The Analyst, vol. 122, p. 119-124, Oct. 1997.
Elie, et al., Sleep latency is shortened during 4 weeks of treatment with zaleplon, a novel nonbenzodiazapine hypnotic. Journal Clin Psychiatry vol. 60, No. 8, p. 536-544, Aug. 1999.
Giroud, et al., Determination of zaleplon and zolpidem by liquid chromatography-turbo-ionspray mass sspectrometry: application to forensic cases. Journal of Chromatography B. vol. 789, p. 131-138, 2003.
Horstkotter, et al., Separation and identification of zaleplon metabolites in human urine using capillary electrophoresis with laser induced fluorescence detection and liquid chromatography-mass spectrometry. Journal of Chromatography A, vol. 1014, p. 71-81, 2003.
Huynh, et al., Development of a homogeneous immunoassay for the detection of zolpidem in urine. Journal of Analytical Toxicology, vol. 33, p. 486-490, Oct. 2009.
Journal of Clinical Chemistry, Table of Contents, vol. 55(6), pp. 1051-1258, Jun. 2009.
Neubauer, DN. Indeplon: the development of a new hypnotic, Expert Opin. Investig. Durgs, 14(10):1269-1276, Oct. 2005.
Rosen, et al.. Zaleplon Pharmacokinetics and Absolute Bioavailability. Biopharmaceutics & Drug Disposition, vol. 20, p. 171-175, Apr. 1999.
Zhang, et al., High performance liquid chromatography-atomospheric pressure chemical ionisation-mass spectrometry determination of zaleplon in human serum. Journal of Pharmaceutical and Biomedical Analysis, vol. 40, p. 707-714, 2006.

* cited by examiner

*Primary Examiner* — Shafiqul Haq
*Assistant Examiner* — Galina Yakovleva
(74) *Attorney, Agent, or Firm* — Hueschen and Sage (57) ABSTRACT

The invention relates to novel immunogens, antibodies, methods and kits for use in immunoassays to detect and quantify zaleplon, metabolites of zaleplon and indiplon. These are the first described immunoassays for these compounds and have greater sensitivity than alternative analytical techniques.

17 Claims, 3 Drawing Sheets

IMMUNODETECTION AND QUANTIFICATION OF PYRAZOLOPYRIMIDINE SEDATIVES

FIELD OF THE INVENTION

The invention, in the immunoassay field, provides a solution to the problem of a lack of a practical, economic and sensitive analytical test for zaleplon and related pyrazolopyrimidines.

BACKGROUND TO THE INVENTION

The pyrazolopyrimidine zaleplon is a short-acting, benzodiazepine-like sedative/hypnotic used for the treatment of insomnia (Elie et al 1999). Following oral administration it is rapidly absorbed, the blood concentration peaking after approximately one hour (UKMI monograph 2000). It has a half-life of approximately one hour and is primarily metabolized by aldehyde oxidase and to a lesser extent by CYP3A4, the majority of a single dose being eliminated in urine as 5-oxozaleplon, 5-oxo-N-desethylzaleplon and 5-oxozaleplon glucuronide, while less than 1% is excreted unchanged. The closely related analogue, indiplon, has similar properties. Because of its rapid action and short half-life, zaleplon is increasingly finding use in drug-facilitated crimes (e.g. robbery, sexual assault, mugging) and recreational abuse, hence methods are required for the detection of zaleplon and indiplon. Horstkötter et al. (2003) described a capillary electrophoresis method for detection of zaleplon and metabolites in urine following solid-phase extraction, with detection limits of 10 ng/ml for zaleplon and N-desethylzaleplon and 100 ng/ml for 5-oxozaleplon and 5-oxo-N-desethylzaleplon Zhang et al. (2006) described a HPLC-MS method for detection of zaleplon in human plasma, with a detection limit of 0.1 ng/ml.

Specific binding reactions, such as antibody-antigen interactions, have been used extensively in immunoassays to detect a variety of substances present in biological samples. Compared to methods such as HPLC and LC-MS, such methods are less costly, require non-specialist staff for implementation and can be applied outside of the laboratory e.g. incorporated into a dipstick device. Thus, radioimmunoassays (RIAs) could be used for the determination of zaleplon, indiplon and their metabolites. Radioimmunoassays are very sensitive, but do require radionuclide tracers, for example $^{125}I$ and $^{3}H$. Enzyme-linked immunosorbent assays (ELISAs) are a non-radioactive alternative that could be used for their qualitative and quantitative determination. There are no known RIAs or ELISAs for zaleplon, indiplon or their metabolites.

Immunoassays for the sensitive and specific determination of zaleplon and/or indiplon are desirable for application in therapeutic, toxicological and clinical settings. The invention described herein reports for the first time the development of two highly sensitive polyclonal antibodies for the detection of zaleplon, its metabolites and indiplon. The invention further describes methods and kits for the detection of zaleplon, its metabolites and the related pyrazolopyrimidine indiplon.

SUMMARY OF THE INVENTION

The invention provides a practical, economic and sensitive analytical test for zaleplon, its metabolites and related pyrazolopyrimidines. Novel, high affinity antibodies derived from novel immunogens with a limit of detection in the picogram range enable an assay for zaleplon and its analogues with an extended window of detection.

DETAILED DESCRIPTION OF THE INVENTION

Figure 1:
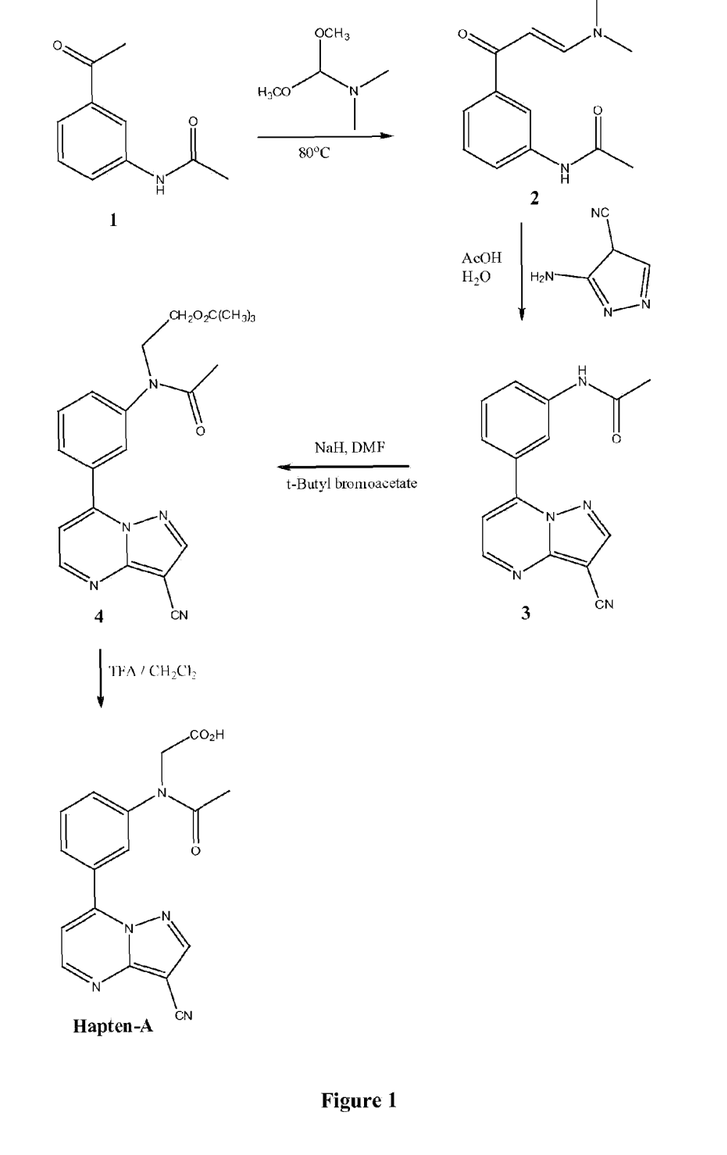
FIG. 1 Synthesis of Hapten-A
FIG. 2 Synthesis of Hapten-B and Hapten-C
FIG. 3 Structures of zaleplon, 5-oxozaleplon and indiplon
Figure 2:
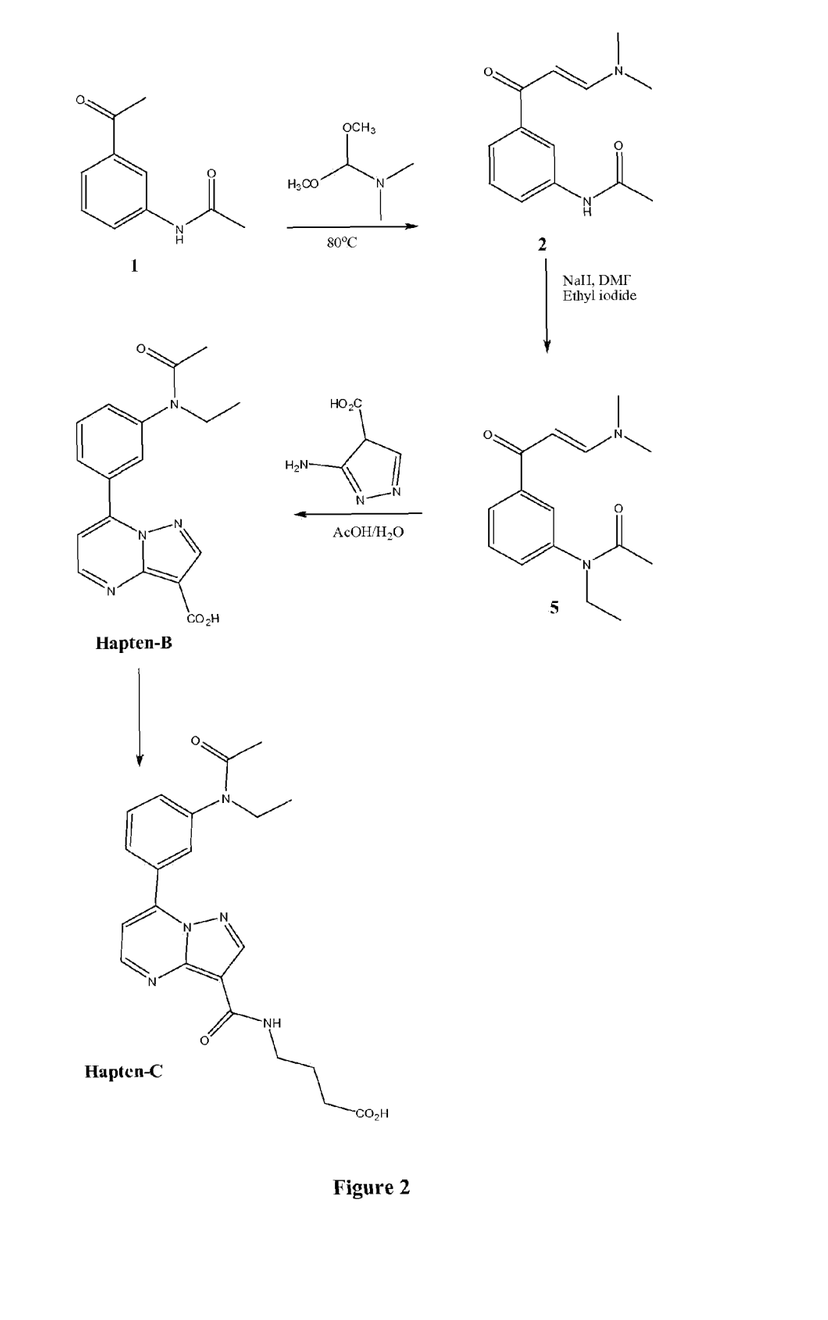
Figure 3:
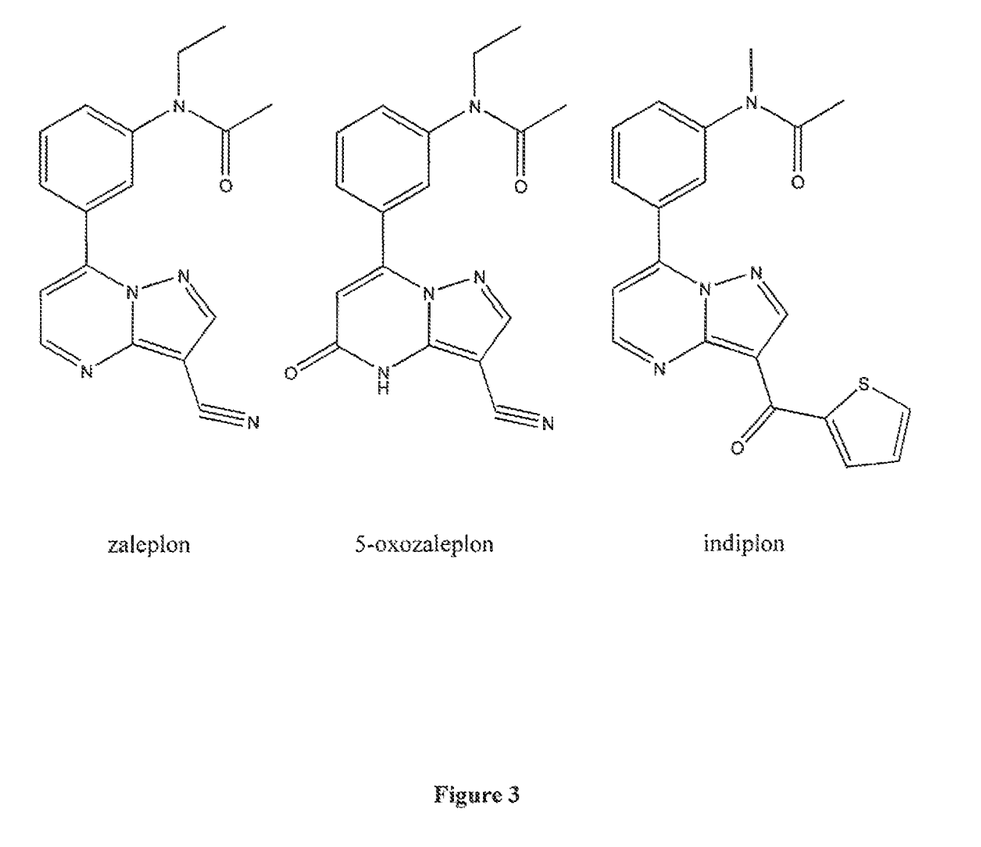

The invention, in the immunoassay field, provides a solution to the problem of a lack of a practical, economic and sensitive analytical test for zaleplon, its metabolites and related pyrazolopyrimidines such as indiplon. The rapid metabolism of zaleplon ensures that its detection in biological fluids is beyond the detection limits of conventional, impractical and uneconomical analytical techniques such as LC and LC-MS within approximately 24 hours of drug ingestion. The lower limit of detection of these techniques using standard laboratory equipment is normally approximately 1 ng/ml. However, the Inventors disclose a zaleplon-specific antibody with an $IC_{50}$ of 63 pg/ml, which equates to a lower limit of detection of <1 pg/ml. Compared to current analytical tests such as the LC-MS method of Zhang et al (2006), which reports a plasma detection limit of 100 pg/ml, the zaleplon-specific antibody considerably extends the detection window of zaleplon in biological fluids. This extension of the detection window could be critical in the case of drug-facilitated rapes. Therefore, a first aspect of the invention is an immunogen of the structure Structure I where n=0 or 1. When n=1, the crosslinker joins the carbonyl substituent to the accm, an antigenicity-conferring carrier material. The crosslinker, is preferably —X—Y—Z—, where X is a heteroatom, preferably nitrogen, oxygen or sulphur; Y is a $C_1$-$C_{10}$, preferably a $C_2$-$C_6$, substituted or unsubstituted straight chain alkylene moiety, or arylene moiety; Z (before conjugation with the accm) is selected from a carboxy, a dithiopyridyl, a maleimide, an amino, a hydroxyl, a thiol, a thioester or an aldehyde moiety, most preferably a carboxy moiety. Advantageously, Z, before conjugation with an antigenicity-conferring material to produce an immunogen, is selected from a carboxylic acid, a dithiopyridyl, a maleimide, amino, hydroxyl, thiol, thioester or an aldehyde moiety. Where Z, before conjugation to the antigenicity-conferring material is a carboxylic acid (COOH), the oxygen of the hydroxyl group combines first with DCC and then NHS to form an ester with a powerful leaving group. Nucleophilic attack on the carbonyl group (C=O) of the ester functionality by a free amine group on the antigenicity-conferring material results in an amide bond and formation of the desired immunogen. A general definition of crosslinker is a reagent with two or more reactive groups capable of reacting with and therefore 'linking' two or more molecules. Commonly, if the crosslinker has two reactive groups they are usually at opposite ends of the molecule, and the crosslinker is referred to as bifunctional. For the purposes of this invention the two molecules are a hapten and an accm such as bovine thyroglobulin (BTG) or a hapten and a detectable labelling agent such as horseradish peroxidase (HRP). The skilled reader is referred to Bioconjugate Techniques G. Hermanson, ed., Academic Press, 1996, for details of the interaction between the reactive groups and antigenicity-conferring carrier materials/detectable labelling agents. The accm can be any material that makes the hapten-accm molecule immunogenic. For example the accm can be a protein, a protein fragment, a synthetic polypeptide or a semi-synthetic polypeptide. The preferred immunogen is where n=0 and the accm is BTG i.e. the immunogen is made up of BTG attached, via an amino group, directly to the carbonyl group of structure I.

A second aspect of the invention is an antibody, raised against the immunogen of structure I that binds to an epitope of zaleplon. The antibody is preferably for use in detecting or determining zaleplon in a solution or in an in vitro sample taken from a patient. The antibody can be a monoclonal antibody, but is preferably a polyclonal antibody.

A third aspect of the invention is a method of detecting or determining zaleplon in a solution or an individual, the method comprising contacting an in vitro sample taken from the individual or the solution with a conjugate, and an antibody that binds to an epitope of zaleplon, detecting the bound conjugate, and deducing from calibration values the presence of or amount of zaleplon.

A fourth aspect of the invention is a kit for detecting or determining zaleplon, the kit comprising an antibody that binds to an epitope of and is substantially specific for zaleplon. Substantially specific implies that the antibody has a cross-reactivity towards analytes compared to zaleplon of less than 10%, preferably less than 5%, most preferably less than 1%. The antibody is further characterised by being raised to an immunogen of structure I. The kit may optionally include instructions for the use of said antibody and any other additional components included in the kit, for detecting or determining zaleplon. Conjugates and calibrators are examples of other additional components.

It has been reported that seventy percent of an administered dose of zaleplon was recovered in urine within 48 hours (71% recovered within 6 days), almost all as zaleplon metabolites, such as 5-oxozaleplon. This suggests that for long-term detection (>1-2 days) of zaleplon ingestion, an immunoassay able to detect the main metabolite 5-oxozaleplon is desirable. To acquire antibodies that detect 5-oxozaleplon, zaleplon suitably functionalised at the 5-positon of the pyrazolopyrimidine heterocycle would be the methodology adopted by the skilled person. This would enable attachment of the accm through the 5-position and following immunisation of a host such as a sheep or rabbit, antibodies that recognise zaleplon and 5-oxozaleplon would be expected. The problem of this method is the synthesis of zaleplon functionalised at the 5-position. Such a molecule would either require either a resource intensive synthetic route or implementation of a novel 'one-pot', synthetic methodology, achievable through informed trial and error. For example, an enzymatic synthesis could be effected using aldehyde oxidase and zaleplon but this would require isolation or expression of the protein. The Inventors overcame this impediment by forming the immunogen by derivatising the 3-cyano group of zaleplon followed by accm attachment. It was reasoned that derivatisation and accm conjugation at this position would shield one side of the pyrazolopyrimidine heterocycle from antibody-binding (positions 2, 3, 4 and 5 of the pyrazolopyrimidine) and thus promote antibody recognition of the 3-(N-alkylacetamido)phenyl substituent of zaleplon which is located on the opposite side of the heterocycle at position 7. This has been confirmed by the recognition of indiplon by the antibody (see Table 2).

A further aspect of the invention is an immunogen of the structure

Structure II where n=0 or 1. When n=1, the crosslinker joins the carbonyl substituent attached to the fused heterocycle to the accm, an antigenicity-conferring carrier material. The crosslinker, is preferably —X—Y—Z—, where X is a heteroatom, preferably nitrogen, oxygen or sulphur; Y is a $C_1$-$C_{10}$, preferably a $C_2$-$C_6$, substituted or unsubstituted straight chain alkylene moiety, or arylene moiety; Z (before conjugation with the accm) is selected from a carboxy, a dithiopyridyl, a maleimide, an amino, a hydroxyl, a thiol, a thioester or an aldehyde moiety, most preferably a carboxy moiety. The antigenicity-conferring carrier material (accm) can be any material that makes the hapten-accm molecule immunogenic. For example the accm can be a protein, a protein fragment, a synthetic polypeptide or a semi-synthetic polypeptide. The preferred immunogen is where n=1, X is nitrogen, Y is propylene, Z (after conjugation with the accm) is carbonyl and the accm=BTG.

Another aspect of the invention is an antibody, raised against the immunogen of structure II that binds to an epitope of zaleplon and indiplon; preferably the antibody binds to an epitope of one or more of zaleplon, 5-oxozaleplon and indiplon. The antibody is for use in detecting or determining zaleplon and/or indiplon in a solution or in an in vitro sample taken from a patient; preferably the antibody is for use in detecting or determining one or more of zaleplon, 5-oxozaleplon and indiplon, in a solution or in an in vitro sample taken from a patient. The antibody can be a monoclonal antibody, but is preferably a polyclonal antibody. As the antibody recognizes more than one analyte, unless the analyte to be measured in a solution or a sample taken from a patient is known to be a single analyte, determining in this case means quantification in terms of calibrator equivalents i.e. if zaleplon and indiplon are known to be present in the solution or in vitro sample to be analysed, individual quantification is not possible and only a calibrator-equivalent amount of zaleplon plus indiplon can be calculated. Another aspect of the invention is a method of detecting or determining zaleplon and/or indiplon in a solution or an in vitro sample taken from an individual, the method comprising contacting an in vitro sample or the solution with one or more conjugates, and an antibody that binds to an epitope of zaleplon and indiplon, detecting the bound conjugate(s), and deducing from calibration values the presence of or amount of zaleplon and/or indiplon, the amount being quantified in calibrator equivalents; a preferred method is for detecting or determining one or more of zaleplon, 5-oxozaleplon and indiplon in a solution or an in vitro sample taken from an individual, the method comprising contacting an in vitro sample or the solution with one or more conjugates, and an antibody that binds to an epitope of zaleplon, 5-oxozaleplon and indiplon, detecting the bound conjugate(s), and deducing from calibration values the presence of or amount of one or more of zaleplon, 5-oxozaleplon and indiplon, the amount being quantified in calibrator equivalents.

A final aspect of the invention is a kit for detecting or determining zaleplon and/or indiplon, the kit including an antibody that binds to an epitope of zaleplon and indiplon; preferably the kit is for detecting or determining one or more of zaleplon, 5-oxozaleplon and indiplon, the kit including an antibody that binds to an epitope of zaleplon, 5-oxozaleplon and indiplon. The antibody is further characterised by being raised to an immunogen of structure II. The kit may optionally include instructions for the use of said antibody and any other additional components included in the kit, for detecting or determining zaleplon and/or indiplon, preferably one or more of zaleplon, 5-oxozaleplon and indiplon. Conjugates and calibrators are examples of other additional components.

For the purposes of the invention, the solution may be, for example, a solution of cultured cells. A solution of the appropriate cultured cells would enable an in vitro assay to test for, for example, metabolic products and drug activity. The sample can be any peripheral biological fluid such as plasma or serum but is preferably urine. The conjugate(s) of the method and kit (if included) are made up of haptens attached to labelling agents. The hapten(s) of the conjugate(s) are molecules that can bind to the antibodies of the method. The use of haptens, conjugates and antibodies in the context of immunoassays is well known in the art.

Preferably, the labelling agent of the conjugate(s) is selected from an enzyme, a luminescent substance, a radioactive substance, or a mixture thereof. More preferably, the labelling agent is an enzyme, preferably a peroxidase, most preferably horseradish peroxidase (HRP). Alternatively, or additionally, the luminescent substance may be a bioluminescent, chemiluminescent or fluorescent material.

Methods, Examples and Results

Preparation of Haptens, Immunogens and Conjugates

Although haptens provide defined structural epitopes, they are not in themselves immunogenic and therefore need to be conjugated to carrier materials, which will elicit an immunogenic response when administered to a host animal. Appropriate carrier materials commonly contain poly(amino acid) segments and include polypeptides, proteins and glycoproteins. Illustrative examples of useful carrier materials are bovine serum albumin (BSA), egg ovalbumin, bovine gamma globulin, bovine thyroglobulin (BTG), keyhole limpet haemocyanin (KLH) etc. Alternatively, synthetic poly(amino acids) having a sufficient number of available amino groups, such as lysine, may be employed, as may other synthetic or natural polymeric materials bearing reactive functional groups. In particular, carbohydrates, yeasts or polysaccharides may be conjugated to the hapten to produce an immunogen. The haptens can also be coupled to a detectable labelling agent such as an enzyme (for example, horseradish peroxidase), a substance having fluorescent properties or a radioactive label for the preparation of conjugates (or detection reagents) for use in the immunoassays. The fluorescent substance may be, for example, a monovalent residue of fluorescein or a derivative thereof. Immunogen formation often involves conventional conjugation chemistry such as the oxygen of a hydroxyl group combining first with DCC and then NHS to form an ester with a powerful leaving group. Nucleophilic attack on the carbonyl of the ester functionality by an amine group on the protein (BSA or BTG), results in an amide bond and formation of an immunogen. In order to confirm that adequate conjugation of hapten to carrier material has been achieved, prior to immunisation, each immunogen is evaluated using matrix-assisted UV laser desorption/ionisation time-of-flight mass spectroscopy (MALDI-TOF MS).

General Procedure for MALDI-TOF Analysis of Immunogens.

MALDI-TOF mass spectrometry was performed using a Voyager STR Biospectrometry Research Station laser-desorption mass spectrometer coupled with delayed extraction. An aliquot of each sample to be analysed was diluted in 0.1% aqueous trifluoroacetic acid (TFA) to create 1 mg/ml sample solutions. Aliquots (1 µl) were analysed using a matrix of sinapinic acid and bovine serum albumin (Fluka) was used as an external calibrant.

Preparation of Antisera

In order to generate polyclonal antisera, the immunogen of the present invention is mixed with Freund's adjuvant and the mixture is injected into a host animal, such as rabbit, sheep, mouse, guinea pig or horse. Further injections (boosts) are made and serum is sampled for evaluation of the antibody titre. When the optimal titre has been attained, the host animal is bled to yield a suitable volume of specific antiserum. The degree of antibody purification required depends on the intended application. For many purposes, there is no requirement for purification, however, in other cases, such as where the antibody is to be immobilised on a solid support, purification steps can be taken to remove undesired material and eliminate non-specific binding.

Immunoassay Development

The process of developing an immunoassay is well known to the person skilled in the art. Briefly, for a competitive immunoassay in which the target analyte is a non-immunogenic molecule commonly referred to as a hapten, the following process is conducted: antibodies are produced by immunising an animal, preferably a mammalian animal, by repeated administration of an immunogen. The serum from the immunised animal is collected when the antibody titre is sufficiently high. A conjugate is added to a sample containing the target analyte and the raised antibodies, and the conjugate and analyte compete for binding to the antibodies. The process may comprise fixing said serum antibodies to a backing substrate such as a polystyrene solid support or a biochip. The antibodies can be polyclonal or monoclonal. The signal emitted in the immunoassay is proportionate to the amount of conjugate bound to the antibodies which in turn is inversely proportionate to the analyte concentration. The signal can be detected or quantified by comparison with a calibrator.

Example 1

Synthesis of N-{3-[3-(Dimethylamino)-1-oxo-2-propenyl]phenyl}acetamide 2

To a solution of dimethylformamide dimethylacetal (50 ml) was added N-(3-acethylphenyl)acetamide 1 (15 g, 0.085 mol) and the mixture was heated at reflux overnight. The solution was evaporated to dryness and the residue obtained was taken up in dichloromethane (200 ml), dried over sodium sulfate, filtered and concentrated to dryness to give the title compound 2 (15.8 g) as a yellow oil.

Example 2

Preparation of N-[3-[3-(Cyanopyrazolo[1,5-a]pyrimidin-7-yl)phenyl]ethyl-acetamide 3

A mixture N-[3-[3-(Dimethylamino)-1-oxo-2-propenyl]phenyl]acetamide 2 (11.61 g, 0.05 mol) and 3-amino-4-pyrrazolecarbonitrile (5.7 g, 0.053 mol) in a mixture of acetic acid (85 ml) and water (50 ml) was heated at 50° C. for two hours, after this time the solution became a white solid. After cooling to room temperature, water (100 ml) was added and the solid was recovered by filtration, washed with water and dried.

The solid was suspended again in a mixture of acetone and hexane (1:1) (200 ml) and stirred for 30 minutes, filtered and dried to give compound 3 (15.2 g) as a white solid.

Example 3

Preparation of N-[3-(3-Cyanopyrazolo[1,5-a]pyrimidin-7-yl)phenyl]-N-tert-butylacetylacetamide 4

To a solution of N-[3-(3-Cyanopyrazolo[1,5-a]pyrimidin-7-yl)phenyl]-N-ethyl-acetamide 3 (5.5 g, 0.02 mol) in DMF (150 ml) under nitrogen was added sodium hydride (60% in oil) (960 mg, 0.024 mol) and mixture stirred was heated at 60° C. for 30 minutes. The mixture was then cooled to room temperature and to this a solution of tert-butyl bromoacetate (4.68 g, 0.024 mol) in DMF (50 ml) was added dropwise. The mixture was then stirred and heated at 60° C. for 6 hours. The solution was then concentrated to dryness, water was added (200 ml) and the solution was extracted with ethyl acetate (2×200 ml). The combined ethyl acetate extracts were washed with water (100 ml) and brine (100 ml), dried over sodium sulfate, filtered and concentrated to dryness. The crude product obtained was purified by chromatography on silica gel (chloroform/methanol: 95/5) to give the ester 4 as a yellow solid (3.2 g). NMR$^{13}$C: 173.6, 170.2, 155.1, 153.2, 148.9, 148.7, 145.2, 133.1, 132.5, 131.8, 131.1, 131.02, 114.2, 112.1, 83.6, 79.8, 31.9, 28.7 and 22.8.

Example 4

Preparation of N-[3-(3-Cyanopyrazolo[1,5-a]pyrimidin-7-yl)phenyl]-N-carboxymethylacetamide (Hapten-A)

To a solution of N-[3-(3-cyanopyrazolo[1,5-a]pyrimidin-7-yl)phenyl]-N-tert-butylacetylacetamide 4 (9.0 g, 0.023 mol) in dichloromethane (200 ml) was added trifluoroacetic acid (60 ml). The reaction mixture was stirred at room temperature for four hours. The solution was concentrated to dryness. The crude product obtained was purified by chromatography on silica gel using chloroform/methanol (9/1). 5.5 g of Hapten-A was obtained as a foamy solid. NMR$^{13}$C: 172.7, 172.2, 153.1, 151.6, 147.6, 147.2, 143.7, 131.56, 131.2, 131.0, 129.8, 112.9, 110.4, 84.1, 51.6, 29.5 and 22.6

Example 5

Conjugation of Hapten-A to Bovine Serum Albumin (BSA)

To a solution of Hapten-A (15.12 mg, 0.045 mmol) in DMF (1 ml) was added N,N-dicyclohexylcarbodiimide (DCC) (10.23 mg, 0.0496 mmol) and N-hydroxysuccinimide (NHS) (5.7 mg, 0.0496 mmol) and the mixture was stirred at room temperature overnight. The dicyclohexylurea formed was removed by filtration and the solution was added dropwise to a solution of BSA (50 mg) in 50 mM sodium bicarbonate solution (pH 8.5) (5 ml). The mixture was then stirred overnight at 4° C. The solution was then dialysed against 50 mM phosphate buffer pH 7.2 (3×10 L) for 24 hours at 4° C., and freeze-dried. Maldi results showed 16.83 molecules of Hapten-A had been conjugated to one molecule of BSA.

Example 6

Conjugation of Hapten-A to BTG to Form Immunogen A

To a solution of Hapten-A (52.64 mg, 0.0157 mmol) in DMF (1 ml) was added N,N-dicyclohexylcarbodiimide (DCC) (35.48, 0.172 mmol) and N-hydroxysuccinimide (NHS) (19.8 mg, 0.172 mmol) and the mixture was stirred at room temperature overnight. The dicyclohexylurea formed was removed by filtration and the solution was added dropwise to a solution of BTG (150 mg) in 50 mM sodium bicarbonate solution (pH 8.5) (5 ml). The mixture was then stirred overnight at 4° C. The solution was then dialysed against 50 mM phosphate buffer pH 7.2 (3×10 L) for 24 hours at 4° C., and freeze-dried.

Example 7

Conjugation of Hapten-A to HRP

EDC hydrochloride (10 mg) was dissolved in water (0.5 ml) and immediately added to a solution of Hapten-A (2 mg) in DMF (0.2 ml). After mixing, this solution was added dropwise to a solution of HRP (20 mg) in water (1 ml). Sulfo-NHS (5 mg) was added and the reaction mixture was incubated in the dark at room temperature overnight. Excess hapten was removed with double PD-10 columns (Pharmacia) in series, pre-equilibrated with PBS at pH 7.2. The hapten-HRP conjugate was then dialysed overnight against 10 L of PBS at pH 7.2 at 4° C.

Example 8

Preparation of N-{3-[3-(dimethylamino)-1-oxo-2-propenyl]phenyl}-N-ethylacetamide 5

A mixture of N-{3-[3-(dimethylamino)-1-oxo-2-propenyl]phenyl}acetamide 2 (12.7 g, 0.055 mol) and sodium hydride (60% in oil) (2.5 g) in DMF (150 ml) under nitrogen was stirred at room temperature for 30 minutes. The solution was then cooled to 0° C., and a solution of ethyl iodide (9.38 g, 0.063 mol) in DMF (50 ml) was added slowly dropwise. The mixture was then stirred at room temperature for one hour. The DMF was removed under high vacuum, water (200 ml) was added to the residue and the mixture was extracted with ethyl acetate (2×200 ml). The combined ethyl acetate extracts were washed with water (150 ml) and brine (100 ml), dried over sodium sulfate, filtered and concentrated to dryness to give the crude product. Compound 5 was obtained after recrystallization from hexane (7.9 g). M. P. (Hexane): 109-112° C.

Example 9

Preparation of 7-[3-(N-ethylacetamido)phenyl]carboxypyrazolo[1,5-a]pyrimidinyl-3-carboxylic acid (Zaleplon-3-carboxylic acid) (Hapten-B)

A mixture of Compound 5 (7.65 g, 0.03 mol) and 4H-3-aminopyrazole-4-carboxylic acid (3.75 g, 0.03 mol) in acetic acid (51 ml) and water (30 ml) was stirred and heated at 50° C. for 3 hours. Water (100 ml) was added to the solution and the mixture allowed to cool to 10° C. The resulting crystals were washed and dried overnight to give the Zaleplon-3-carboxylic acid (Hapten-B) as a white solid (5.7 g).

Example-10

Preparation of 5-aza-6-{7-[3-(N-ethylacetamido)phenyl]carboxypyrazolo[1,5-a]pyrimidin-3-yl}-6-oxo-hexanoic acid (Hapten-C)

To a solution of Hapten-B (4.32 g, 13.2 mmol) in DMF (50 ml) was added ethyl 4-aminobutyrate hydrochloride (3.24 g, 19.8 mmol), pyridine (4 ml) and EDC.HCl (3.78 g, 19.8 mmol) respectively and the mixture was stirred at room temperature for 4 hours. The solution was then evaporated to dryness, water added (100 ml) and the solution was made alkaline (pH 9) by the addition of 50 mM potassium carbonate. The solution was then extracted with ethyl acetate (3×100 ml), the combined organic phases washed and the solution dried over sodium sulphate. The crude product was purified by chromatography on silica gel using chloroform/methanol (90/10) to give the intermediate ester (5.2 g).

To a solution of the ester (5.2 g, 11.9 mmol) in THF (100 ml) and water (100 ml) was added potassium hydroxide (2.0 g, 35.7 mmol) and the mixture was stirred at room temperature overnight. The THF was removed and the aqueous solution acidified to pH 2 by HCl (1N). The solution was then extracted with dichloromethane (3×100 ml). The combined organic phases were washed with water (100 ml), dried over sodium sulphate, filtered and concentrated to dryness. The crude product obtained was purified by chromatography on silica gel using chloroform/methanol (80/20) to give 2.3 g of Hapten-C.

Example 11

Conjugation of Hapten-C to Bovine Serum Albumin (BSA)

To a cooled solution of Hapten-C (24.56 mg, 0.06 mM) in DMF (3 ml) under nitrogen, was added tri-n-butylanine (15.71 µl, 0.066 mM) and isobutyl chloroformate (IBCF) (8.51 µl, 0.066 mM) and the mixture stirred at 0° C. for 15 min, then 30 min at room temperature. This solution was added dropwise to BSA (50 mg) in sodium bicarbonate (5 ml, 0.1M) and the mixture was stirred overnight at 4° C. The solution was then dialysed against 50 mM phosphate buffer pH 7.2 (3 changes) for 24 hours at 4° C., and freeze-dried. MALDI results showed 26.52 molecule of Hapten-C has been conjugated to one molecule of BSA.

Example 12

Conjugation of Hapten-C to BTG to Form Immunogen C

To a cooled solution of Hapten-C (83.13 mg, 0.203 mM) in DMF (3 ml) under nitrogen was added tri-n-butylanine (53.12 µl, 0.223 mM) and isobutyl chloroformate (IBCF) (28.78 µl. 0.223 mM) and the mixture was stirred at 0° C. for 15 min, then 30 min at room temperature.

The solution was added dropwise to BTG (150 mg) in sodium bicarbonate (5 ml, 0.1M) and the mixture was stirred overnight at 4° C. The solution was then dialysed against 50 mM phosphate buffer pH 7.2 (3 changes) for 24 hours at 4° C., and freeze-dried.

Example 13

Conjugation of Hapten-C to HRP

To a cooled solution of Hapten-C (4 mg) in DMF (200 µl) was added tri-n-butylamine (76 µl) and isobutyl chloroformate (IBCF) (4 µl). The mixture was stirred at 0° C. for 10 minutes and then added dropwise to a cooled solution of HRP (20 mg) in water (800 ml) and the reaction mixture was incubated in the dark at room temperature overnight. Excess hapten was removed with double PD-10 columns (Pharmacia) in series, pre-equilibrated with PBS at pH 7.2. The hapten-HRP conjugate was then dialysed against 10 L of PBS at pH 7.2 at 4° C.

Example 14

Preparation of Antibodies to Immunogens A and C

Aqueous solutions of the immunogens prepared in Examples 6 and 12 were formulated with Freund's Complete Adjuvant (FCA) to form emulsions of Immunogen A and Immunogen [[B]]C in 50% (v/v) FCA. Individual sheep were immunised with the emulsions of Immunogen A and Immunogen C (primary immunisations), 0.25 ml being subcutaneously injected in the flank of each animal. Subsequent boosts of emulsified immunogens in 50% (v/v) Freund's Incomplete Adjuvant (FIA) were at monthly intervals for 1 year. Blood sampling took place 7-14 days after each boost. Each sample was processed to produce antisera which were further purified by caprylic acid and ammonium sulfate precipitated to yield an immunoglobulin G (IgG) fraction. The IgG fraction was evaluated by competitive ELISA microtitre plate assay, as described in Example 15.

Example 15

Development of Competitive ELISA's for Zaleplon, its Metabolites and Derivatives Using Antibodies Raised from Immunogen A The wells of an enhanced binding 96 well polystyrene microtitre plate were coated with the IgG fraction of the antiserum raised to Immunogen A Hapten A-BTG diluted in 10 mM Tris, pH8.5 (125 µl/well). The appropriate antibody coating dilution was determined using standard ELISA chequerboard techniques. The plate was incubated for 2 hours at 37° C., washed 4 times with Tris buffered saline containing Tween 20 (TBST) and tapped dry. Standard solutions of Zaleplon were prepared in TBST at 0, 0.025, 0.05, 0.1, 0.2, 0.4, 0.8, 1.6 ng/ml and standard solutions of its metabolite were prepared in TBST at 0, 0.156, 0.313, 0.625, 1.25, 2.5, 5.0, 10 ng/ml, 50 μl of each was added to the appropriate wells. 75 μl of Conjugate A (Hapten A-HRP), diluted in Tris buffer containing EDTA, D-mannitol, sucrose, thimerosal and BSA, was added to each of the wells. The appropriate dilution of conjugate was also determined using standard ELISA chequerboard techniques. The plate was incubated at 25° C. for 1 hour. The excess unbound conjugate was removed by washing 6 times over a 10 minute period with TBST. 125 μl of tetramethylbenzedine (TMB) substrate solution was added to each well of the plate and incubated for 20 minutes in the dark at room temperature. The reaction was stopped by the addition of 125 μl of 0.2M $H_2SO_4$ to each well. The absorbance was then measured at 450 nm using a microtitre plate reader. The data generated in the assay is presented in Table 1.

TABLE 1

Antibody characterisation assay for zaleplon and indiplon, employing antiserum raised to Immunogen A (Hapten-A-BTG) and Conjugate A (Hapten-A-HRP) as detection reagent.

| Standard concentration | Zaleplon | | Standard concentration | Indiplon | |
|---|---|---|---|---|---|
| ng/ml | $A_{450}$ | % $B/B_0$ | ng/ml | $A_{450}$ | % $B/B_0$ |
| 0.000 | 2.140 | 100 | 0.000 | 2.141 | 100 |
| 0.025 | 1.542 | 72 | 0.156 | 2.063 | 96 |
| 0.050 | 1.180 | 55 | 0.313 | 2.019 | 94 |
| 0.100 | 0.860 | 40 | 0.625 | 1.982 | 93 |
| 0.200 | 0.602 | 28 | 1.250 | 2.112 | 99 |
| 0.400 | 0.406 | 19 | 2.500 | 1.877 | 88 |
| 0.800 | 0.286 | 13 | 5.000 | 1.940 | 91 |
| 1.600 | 0.211 | 10 | 10.000 | 1.931 | 90 |
| $IC_{50}$ (ng/ml) | 0.063 | | $IC_{50}$ (ng/ml) | >10 | |
| % CR | 100 | | % CR | <0.63 | |

$A_{450}$ = absorbance at 450 nm;
B = absorbance at 450 nm;
B0 = absorbance at 450 nm at 0 ng/ml standard concentration;
$IC_{50}$ = standard concentration which produces 50% $B/B_0$;
% CR = percentage cross-reactivity based on specificity to Zaleplon

TABLE 2

Antibody characterisation assay for zaleplon and indiplon, employing antiserum raised to Immunogen C (Hapten-C-BTG) and Conjugate C (Hapten-C-HRP) as detection reagent.

| Standard concentration | Zaleplon | | Standard concentration | Indiplon | |
|---|---|---|---|---|---|
| ng/ml | $A_{450}$ | % $B/B_0$ | ng/ml | $A_{450}$ | % $B/B_0$ |
| 0.000 | 2.278 | 100 | 0.000 | 2.167 | 100 |
| 0.156 | 1.487 | 65 | 0.156 | 1.831 | 84 |
| 0.313 | 1.236 | 54 | 0.313 | 1.664 | 77 |
| 0.625 | 1.021 | 45 | 0.625 | 1.455 | 67 |
| 1.250 | 0.825 | 36 | 1.250 | 1.234 | 57 |
| 2.500 | 0.610 | 27 | 2.500 | 1.006 | 46 |
| 5.000 | 0.457 | 20 | 5.000 | 0.778 | 36 |
| 10.000 | 0.337 | 15 | 10.000 | 0.579 | 27 |
| $IC_{50}$ (ng/ml) | 0.432 | | $IC_{50}$ (ng/ml) | 1.967 | |
| % CR | 100 | | % CR | 22 | |

$A_{450}$ = absorbance at 450 nm;
B = absorbance at 450 nm;
B0 = absorbance at 450 nm at 0 ng/ml standard concentration;
$IC_{50}$ = standard concentration which produces 50% $B/B_0$;
% CR = percentage cross-reactivity based on specificity to Zaleplon

BIBLIOGRAPHY

Elie R., et al. (1999). Sleep latency is shortened during 4 weeks of treatment with zaleplon, a novel nonbenzodiazepine hypnotic. Zaleplon Clinical Study Group. *J. Clin. Psychiatry*, 60(8): 536-544.

Horstkötter C, Schepmann D, Blaschke G. (2003). Separation and identification of zaleplon metabolites in human urine using capillary electrophoresis with laser-induced fluorescence detection and liquid chromatography-mass spectrometry. *J. Chromatogr A*, 1014(1-2): 71-81.

Zaleplon. New Medicines on the Market. UKMI. Monograph. 4/00/13. August 2000.

Zhang B, Zhang Z, Tian Y, Xu F, Chen Y. (2006). High-performance liquid chromatography-atmospheric pressure chemical ionisation-mass spectrometry determination of zaleplon in human plasma. *J Pharm Biomed Anal.*, 40(3): 707-14.

The invention claimed is:

1. A method of detecting or determining an amount of zaleplon in a solution or an in vitro sample taken from an individual, the method comprising:
   (i) contacting the sample or the solution with a conjugate and an antibody raised against an immunogen of the structure:

wherein n=0 or 1, the accm is an antigenicity-conferring carrier material and the crosslinker links a carbonyl group to the accm;
   (ii) detecting the bound conjugate, wherein the conjugate comprises Hapten-A coupled to a detectable labelling agent, wherein the detectable labelling agent is coupled to the carboxylic acid group of Hapten A; and (iii) deducing from calibration value(s) the presence of an amount of zaleplon.

2. The method of claim 1 wherein the detectable labelling agent is selected from the group consisting of an enzyme, a luminescent substance, a radioactive substance, and a mixture thereof.

3. The method of claim 2 wherein the detectable labelling agent is an enzyme.

4. The method of claim 3 wherein the enzyme is a peroxidise.

5. The method of claim 4 wherein the peroxidase is horseradish peroxidase.

6. The method of claim 2 wherein the detectable labelling agent is a luminescent substance.

7. The method of claim 6 wherein the luminescent substance is selected from the group consisting of a bioluminescent, chemiluminescent and fluorescent material.

8. The method of claim 1 wherein the calibration values are produced by using a calibrator, which is zaleplon.

9. The method of claim 1 where the immunogen exhibits n=1, and the crosslinker is —X—Y—Z—, wherein X is a heteroatom; Y is a $C_1$-$C_{10}$, substituted or unsubstituted straight chain alkylene moiety, or arylene moiety; wherein Z (before conjugation with the accm) is selected from a carboxy, a dithiopyridyl, a maleimide, an amino, a hydroxyl, a thiol, a thioester and an aldehyde moiety.

10. The method of claim 1 wherein the immunogen exhibits n=0.

11. The method of claim 1 wherein the antigenicity-conferring material is bovine thyroglobulin.

12. The method of claim 10 wherein the antigenicity-conferring material is bovine thyroglobulin.

13. The method of claim 1 wherein the method has an $IC_{50}$ for zaleplon of <0.1 ng/ml.

14. The method of claim 1 wherein the method has a lower limit of detection of zaleplon of <1 pg/ml.

15. The method of claim 1 wherein the antibody exhibits a cross-reactivity towards indiplon, compared to zaleplon, of less than 10%.

16. The method of claim 1 wherein the antibody exhibits a cross-reactivity towards indiplon, compared to zaleplon, of less than 5%.

17. The method of claim 1 wherein the antibody exhibits a cross-reactivity towards indiplon, compared to zaleplon, of less than 1%.

* * * * *